United States Patent
Kim et al.

(10) Patent No.: US 10,281,396 B2
(45) Date of Patent: May 7, 2019

(54) METHOD AND SYSTEM FOR SIMULTANEOUSLY MEASURING SURFACE NORMAL VECTOR AND SURFACE REFLECTANCE FUNCTION IN MICROSCALE

(71) Applicant: Korea Advanced Institute of Science and Technology, Daejeon (KR)

(72) Inventors: MinHyuk Kim, Daejeon (KR); Giljoo Nam, Daejeon (KR); Joo Ho Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 85 days.

(21) Appl. No.: 15/427,821

(22) Filed: Feb. 8, 2017

(65) Prior Publication Data

US 2018/0087894 A1    Mar. 29, 2018

(30) Foreign Application Priority Data

Sep. 23, 2016  (KR) .......................... 10-2016-0121871

(51) Int. Cl.
| | |
|---|---|
| *G01N 21/55* | (2014.01) |
| *G02B 21/26* | (2006.01) |
| *G02B 21/06* | (2006.01) |
| *G01B 11/24* | (2006.01) |

(52) U.S. Cl.
CPC ............ *G01N 21/55* (2013.01); *G01B 11/24* (2013.01); *G02B 21/06* (2013.01); *G02B 21/26* (2013.01)

(58) Field of Classification Search
None
See application file for complete search history.

(56) References Cited

U.S. PATENT DOCUMENTS

| | | | |
|---|---|---|---|
| 2001/0055733 A1* | 12/2001 | Irie ......................... | G03F 7/201 |
| | | | 430/396 |
| 2004/0041809 A1* | 3/2004 | Thornber ............ | G06K 9/00275 |
| | | | 345/426 |

(Continued)

FOREIGN PATENT DOCUMENTS

| | | |
|---|---|---|
| JP | 2003338448 A | 11/2003 |
| JP | 2013160596 A | 8/2013 |

*Primary Examiner* — Dave Czekaj
*Assistant Examiner* — Tyler W. Sullivan
(74) *Attorney, Agent, or Firm* — Blank Rome LLP

(57) ABSTRACT

Disclosed is a system for simultaneously measuring a surface normal vector and a surface reflection function in microscale. The system includes a light dome having a hemispherical-shaped structure and including LEDs to radiate light to an object placed therein; a macro lens installed camera arranged over the light dome to photograph the object through a hole formed at a center of the light dome under an environment in which a light is radiated from the light dome; an xyz micro-translation stage arranged under the light dome and configured to move in xyz-directions to adjust a focal distance between the macro lens installed camera and the object, and a measurement unit configured to control the light dome and the macro lens installed camera to obtain a microscale image, and configured to simultaneously measure a surface normal vector and a surface reflection function of the object based on the microscale image.

4 Claims, 6 Drawing Sheets

(56) References Cited

U.S. PATENT DOCUMENTS

| | | | |
|---|---|---|---|
| 2008/0147347 A1* | 6/2008 | Shaw | G01B 11/162 702/108 |
| 2012/0155734 A1* | 6/2012 | Barratt | G06T 7/35 382/131 |
| 2012/0212491 A1* | 8/2012 | Hager | G06T 15/04 345/426 |
| 2014/0268160 A1* | 9/2014 | Debevec | G01N 21/55 356/445 |
| 2016/0055632 A1* | 2/2016 | Fu | G01N 21/274 382/129 |

* cited by examiner

METHOD AND SYSTEM FOR SIMULTANEOUSLY MEASURING SURFACE NORMAL VECTOR AND SURFACE REFLECTANCE FUNCTION IN MICROSCALE

CROSS-REFERENCE TO RELATED APPLICATIONS

A claim for priority under 35 U.S.C. § 119 is made to Korean Patent Application No. 10-2016-0121871 filed Sep. 23, 2016, in the Korean Intellectual Property Office, the entire contents of which are hereby incorporated by reference.

BACKGROUND

Embodiments of the inventive concept described herein relate to a method and a system for simultaneously measuring a surface normal vector and a surface reflectance function in microscale, and more particularly, relate to a technique of simultaneously capturing reflectances and normals of spatially various objects in microscale.

In recent years, the study of an accurate description of appearance and normals on a surface of an object, including diffusion, reflection and illumination has been greatly advanced. In this case, the characteristics of the appearance and normals on the surface of an object are greatly dependent on a microscale geometric structure of the object. Microfacet theory of illustrating a surface reflection phenomenon in random irregularity on the level with a microscale geometric structure has been formulated. Due to a very small size of a microfacet, the characteristics of an appearance and a normal on a surface of an object have been stochastically modeled instead of measuring direct distribution.

Meanwhile, the microscale geometric structure is measured based on an image in a graphic work. For example, a microscale geometric structure of a surface of a metal object, which is estimated from reflectance information, is measured by using a profilometer. As another example, information about the appearance of an object obtained from a microscale image is combined with a micro-structure to be modeled.

However, according to the related art, since the appearance and normals of the surface of an object are collected in mutually different schemes, the appearance and normals are not simultaneously collected through one scheme and one system.

Thus, the embodiments of the inventive concept described herein propose a system and a method for simultaneously measuring a microscale surface normal vector and a microscale surface reflection function of an object.

SUMMARY

Embodiments of the inventive concept provide a system and a method for simultaneously measuring a surface normal vector and a surface reflection function of an object in microscale.

In detail, embodiments of the inventive concept provide a system and a method for simultaneously measuring a surface normal vector and a surface reflection function of an object in microscale by photographing the object under spherical harmonics (SH) illumination and pointwise illumination, which uses some LEDs of a light dome as a point light, by means of the light dome including hundreds of LEDs in a structure of a hemispherical shape, a lens installed camera, and an xyz micro-translation stage.

In this case, embodiments of the inventive concept provide a system and a method for preventing a vibration from being generated during obtaining a microscale image.

In addition, embodiments of the inventive concept provide a system and a method for calculating a surface normal vector of an object by using a shape-from specular (SfS) scheme to separate the diffusion and the reflection of a microscale image from each other while the surface normal vector and the surface reflection function of the object are simultaneously measured based on a microscale image.

In addition, embodiments of the inventive concept provide a system and a method for calculating a surface normal vector of an object based on a normal distribution function (NDF) item of reflectance of the object, which is represented as a calculated surface normal vector and a non-parameter function, while the surface normal vector and the surface reflection function of the object are simultaneously measured based on a microscale image.

In addition, embodiments of the inventive concept provide a system and a method for updating a calculated surface reflection function by repeatedly optimizing an NDF item and a geometric structure item representing a shadowing/masking effect in the view direction of a macro lens installed camera.

In addition, embodiments of the inventive concept provide a system and a method for correcting a position of an LED of a light dome with respect to the surface of an xyz micro-translation stage and an axis of a macro lens installed camera on a microscale image which is to be photographed by controlling the light dome and the macro lens installed camera before the microscale image is obtained.

According to an aspect of an embodiment, a system for simultaneously measuring a surface normal vector and a surface reflection function in microscale, which includes: a light dome having a hemispherical-shaped structure and including hundreds of LEDs at compactness of a preset interval to radiate light to an object placed therein; a macro lens installed camera arranged over the light dome to photograph the object through a hole formed at a center of the light dome under an environment in which a light is radiated from the light dome; an xyz micro-translation stage arranged under the light dome and configured to move in xyz-directions to adjust a focal distance between the macro lens installed camera and the object, wherein the object is placed on the xyz micro-translation stage; and a measurement unit configured to control the light dome and the macro lens installed camera to obtain a microscale image by photographing the object under the environment in which the light is radiated from the light dome, and configured to simultaneously measure a surface normal vector and a surface reflection function of the object based on the microscale image.

The measurement unit may obtain the microscale image by photographing the object under spherical harmonics (SH) illumination of the light dome and pointwise illumination that uses at least one of the LEDs of the light dome as a point light, and may calculate the surface normal vector of the object by using a shape-from-specular scheme based on the microscale image.

The measurement unit may measure each initial surface normal vector per pixel of the object in the microscale image and may update the initial surface normal vector by using the SfS scheme based on a mirror-like reflection vector by the point light to calculate the surface normal vector of the object.

The measurement unit may calculate the surface reflection function of the object, based on the calculated surface normal vector, a normal distribution function term of reflectance of the object expressed as a non-parametric function, a geometric structure term representing shadowing/masking effects of the light emitted from the light dome in a view direction of the macro lens installed camera, and a Fresnel term concerned with a color vector.

The measurement unit may update the surface reflection function by repeatedly optimizing the NDF term and the geometric structure item.

The light dome may include the hundreds of the LEDs, each of which is adjusted to plural levels to implement spherical harmonics illumination and coupled to a plano-concave lens to be used as a point light for implementing point-wise illumination.

Before obtaining the microscale image, the measurement unit may control the light dome and the macro lens installed camera such that the measurement unit corrects positions of the LEDs of the light dome and an axis of the macro lens installed camera with respect to a surface of the xyz micro-translation stage on the microscale image to be photographed.

The measurement unit may correct the positions of the LEDs of the light dome with respect to the macro lens installed camera, correct a normal vector of the xyz micro-translation stage with respect to the macro lens installed camera, and transform a view direction of the macro lens installed camera and a vector of light radiated from the light dome to a reference coordinate system of the xyz micro-translation stage.

The system may further include a pneumatic vibration isolation unit which is arranged below the xyz micro-translation stage to prevent at least one of the light dome, the macro lens installed camera and the xyz micro-translation stage from generating a vibration.

According to another aspect of an embodiment, there is provided a method of simultaneously measuring a surface normal vector and a surface reflection function in microscale, wherein the method is performed through a system for simultaneously measuring the surface normal vector and the surface reflection function in microscale. The system includes a light dome having a hemispherical-shaped structure and including hundreds of LEDs at compactness of a preset interval to radiate light to an object placed therein; a macro lens installed camera arranged over the light dome to photograph the object through a hole formed at a center of the light dome under an environment in which a light is radiated from the light dome; and an xyz micro-translation stage arranged under the light dome and configured to move in xyz-directions to adjust a focal distance between the macro lens installed camera and the object, wherein the object is placed on the xyz micro-translation stage. The method includes obtaining a microscale image by controlling the light dome and the macro lens installed camera, wherein the microscale image is obtained by photographing the object under the environment in which the light is radiated from the light dome; and simultaneously measuring a surface normal vector and a surface reflection function of the object based on the microscale image.

The obtaining of the microscale image may include obtaining the microscale image by photographing the object under spherical harmonics (SH) illumination of the light dome and pointwise illumination which uses at least one of the LEDs of the light dome as a point light, and the measuring of the surface normal vector and the surface reflection function may include calculating the surface normal vector of the object by using a shape-from-specular scheme based on the microscale image.

The measuring of the surface normal vector and the surface reflection function may include calculating the surface reflection function of the object, based on the calculated surface normal vector, a normal distribution function term of reflectance of the object expressed as a non-parametric function, a geometric structure term representing shadowing/masking effects of the light emitted from the light dome in a view direction of the macro lens installed camera, and a Fresnel term concerned with a color vector.

According to still another aspect of an embodiment, there is provided a computer program stored in a computer readable medium which is coupled to a computer for implementing a system for simultaneously measuring a surface normal vector and a surface reflection function in microscale to execute a method of simultaneously measuring the surface normal vector and the surface reflection function in microscale, wherein the system includes: a light dome having a hemispherical-shaped structure and including hundreds of LEDs at compactness of a preset interval to radiate light to an object placed therein; a macro lens installed camera arranged over the light dome to photograph the object through a hole formed at a center of the light dome under an environment in which a light is radiated from the light dome; and an xyz micro-translation stage arranged under the light dome and configured to move in xyz-directions to adjust a focal distance between the macro lens installed camera and the object, wherein the object is placed on the xyz micro-translation stage, and wherein the method includes: obtaining a microscale image by controlling the light dome and the macro lens installed camera, wherein the microscale image is obtained by photographing the object under the environment in which the light is radiated from the light dome; and simultaneously measuring a surface normal vector and a surface reflection function of the object based on the microscale image.

According to the embodiments of the inventive concept, the system and the method for simultaneously measuring a surface normal vector and a surface reflection function of an object in microscale may be provided.

In detail, according to the embodiments of the inventive concept, there may be provided the system and the method for simultaneously measuring a surface normal vector and a surface reflection function of an object in microscale by photographing the object under spherical harmonics (SH) illumination and pointwise illumination, which uses some LEDs of a light dome as a point light, by means of the light dome including hundreds of LEDs in a structure of a hemispherical shape, a lens installed camera, and an xyz micro-translation stage.

In this case, according to the embodiments of the inventive concept, the system and the method for preventing a vibration from being generated during obtaining a microscale image may be provided.

In addition, according to the embodiments of the inventive concept, there may be provided the system and the method for calculating a surface normal vector of an object by using a shape-from specular (SfS) scheme to separate the diffusion and the reflection of a microscale image from each other while the surface normal vector and the surface reflection function of the object are simultaneously measured based on a microscale image.

In addition, according to the embodiments of the inventive concept, there may be provided the system and the method for calculating a surface normal vector of an object based on a normal distribution function (NDF) term of reflectance of the object, which is represented as a calculated surface normal vector and a non-parameter function, while the surface normal vector and the surface reflection function of the object are simultaneously measured based on a microscale image.

In addition, according to the embodiments of the inventive concept, there may be provided the system and the method for updating a calculated surface reflection function by repeatedly optimizing an NDF term and a geometric structure term representing a shadowing/masking effect in the view direction of a macro lens installed camera.

In addition, according to the embodiments of the inventive concept, there may be provided the system and the method for correcting a position of a light dome with respect to the surface of an xyz micro-translation stage and an axis of a macro lens installed camera on a microscale image which is to be photographed by controlling the light dome and the macro lens installed camera before the microscale image is obtained.

Therefore, according to the embodiments of the inventive concept, the surface normal vector and the surface reflection function of an object may be simultaneously measured, so that the measurement complexity may be reduced and the measurement accuracy may be improved.

In addition, according to the embodiments of the inventive concept, the over suitability of the process of measuring the surface normal vector and the surface reflection function of an object may be reduced.

Thus, the system for simultaneously measuring a surface normal vector and a surface reflection function of an object according to the embodiments of the inventive concept may be applied to systems for capturing appearances of various objects such as microscope camera systems.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
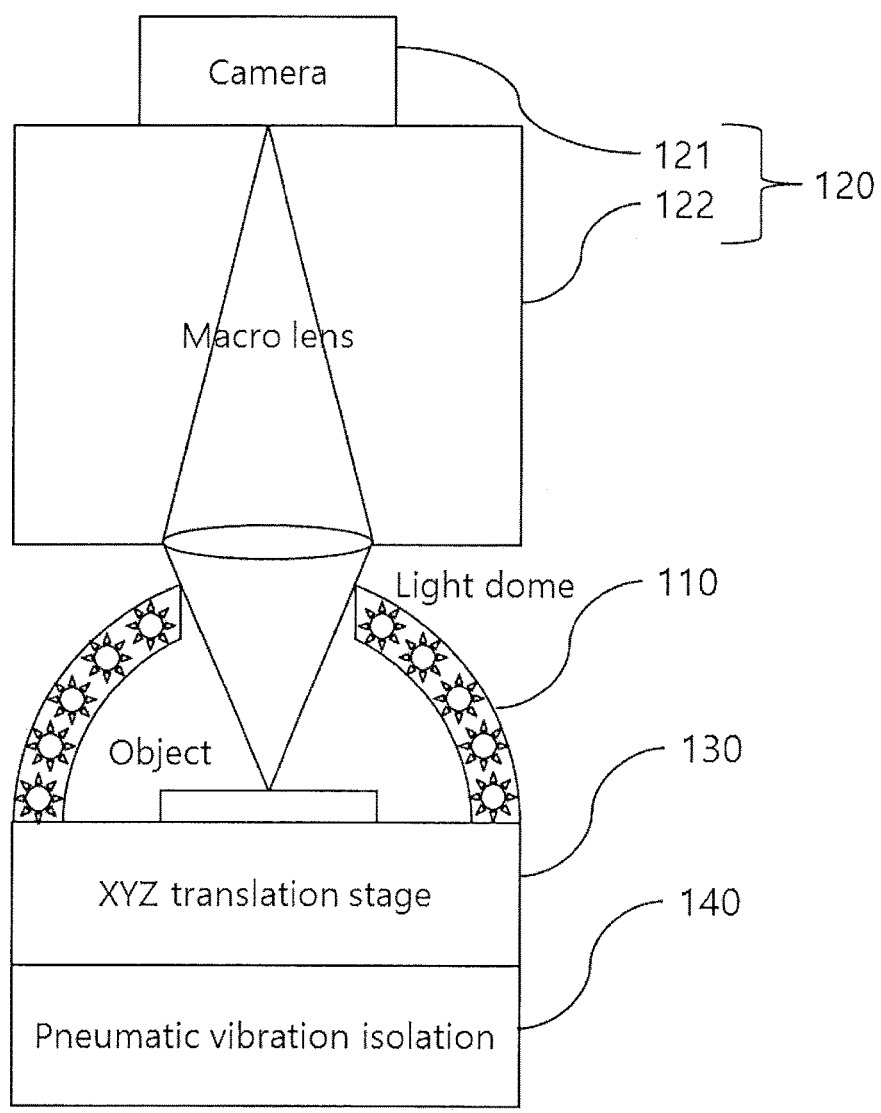
FIGS. 1 to 4 are views illustrating a system for simultaneously measuring a surface normal vector and a surface reflection function in microscale according to an embodiment of the inventive concept.

Hereinafter embodiments of the inventive concept will be described in detail with reference to the accompanying drawings. However, it should be understood that the inventive concept is not limited to the following embodiments. In addition, the same reference numerals used in each drawing represent the same elements.

In addition, terminologies used herein are defined to appropriately describe the exemplary embodiments of the inventive concept and thus may be changed depending on a viewer, the intent of an operator, or a custom. Accordingly, the terminologies must be defined based on the following overall description of this disclosure.

FIGS. 1 to 4 are views illustrating a system for simultaneously measuring a surface normal vector and a surface reflection function in microscale according to an embodiment of the inventive concept. Hereinafter, the system for simultaneously measuring a surface normal vector and a surface reflection function in microscale will be referred to as a "measurement system".

Figure 2:
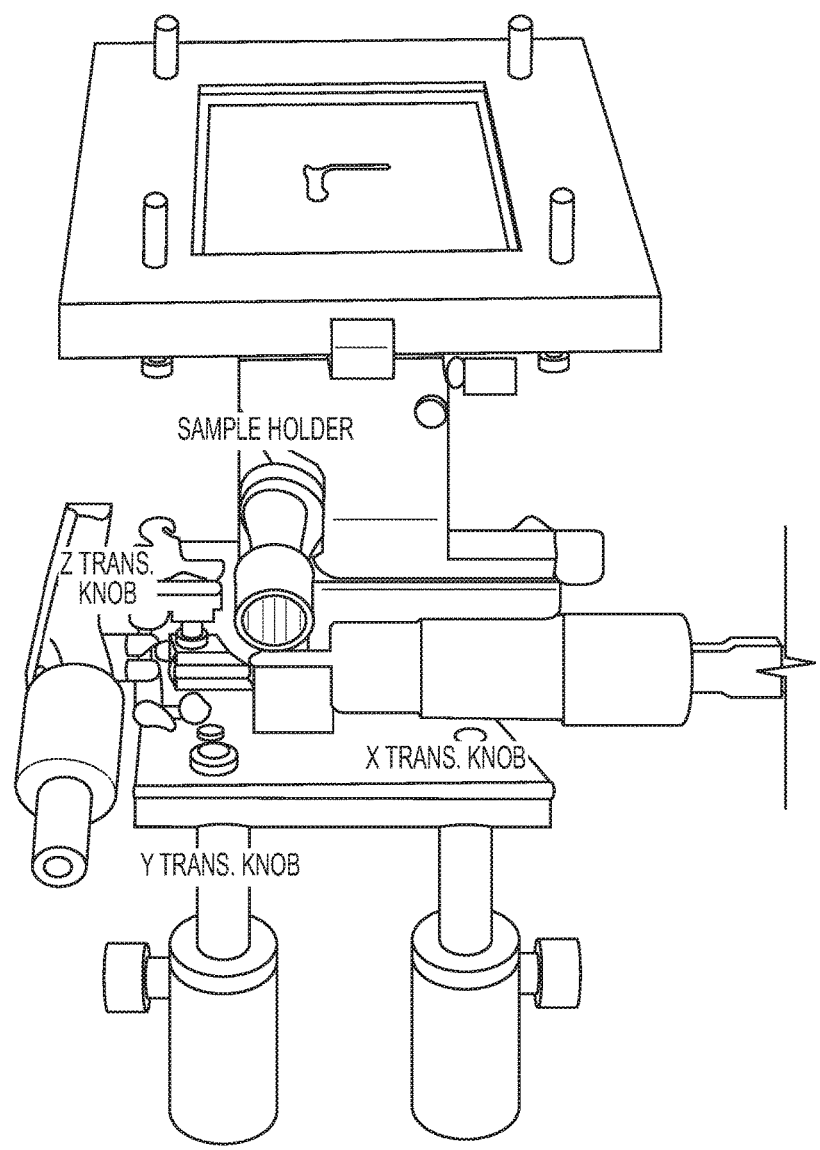
Figure 3:
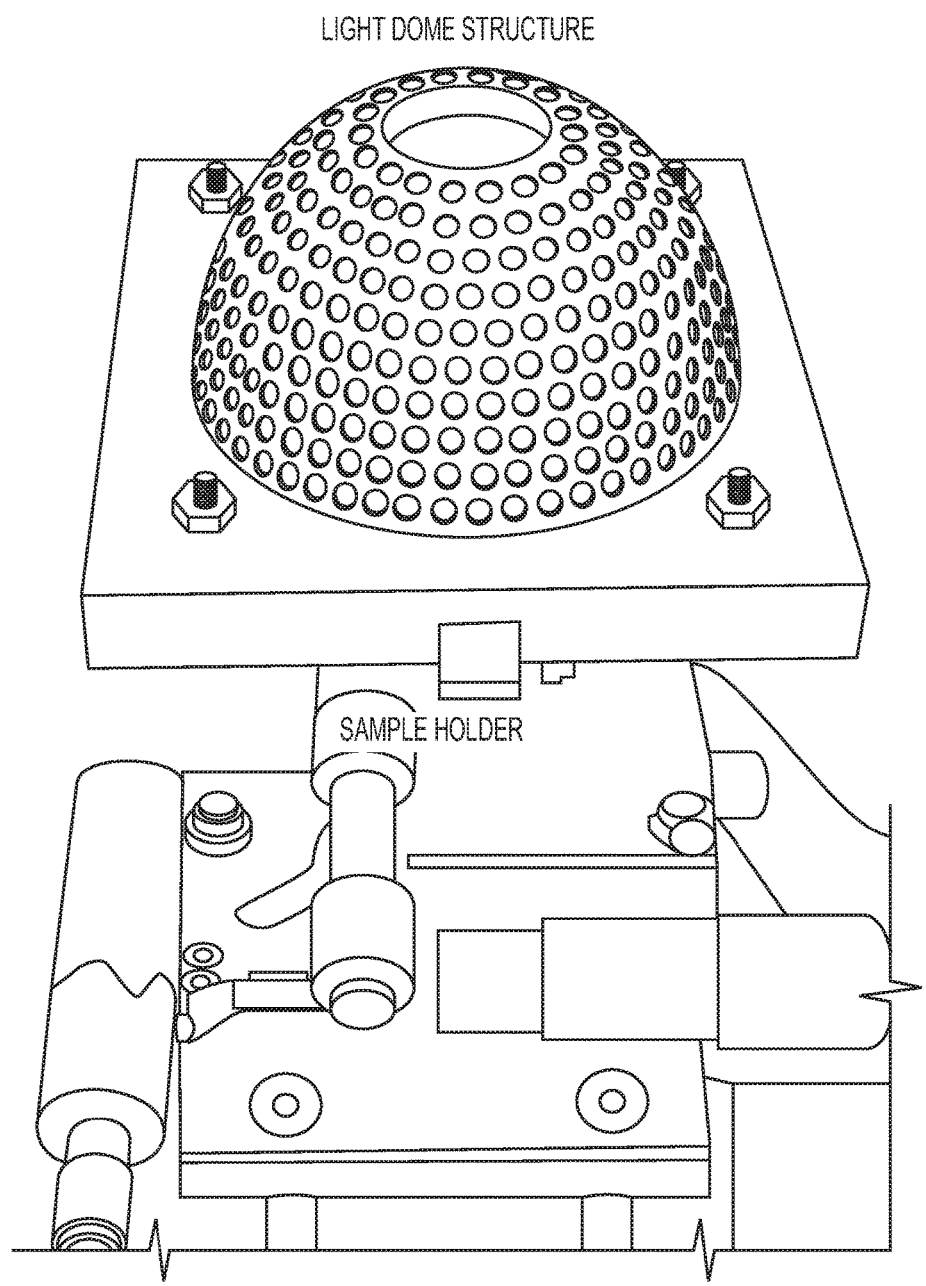
Figure 4:
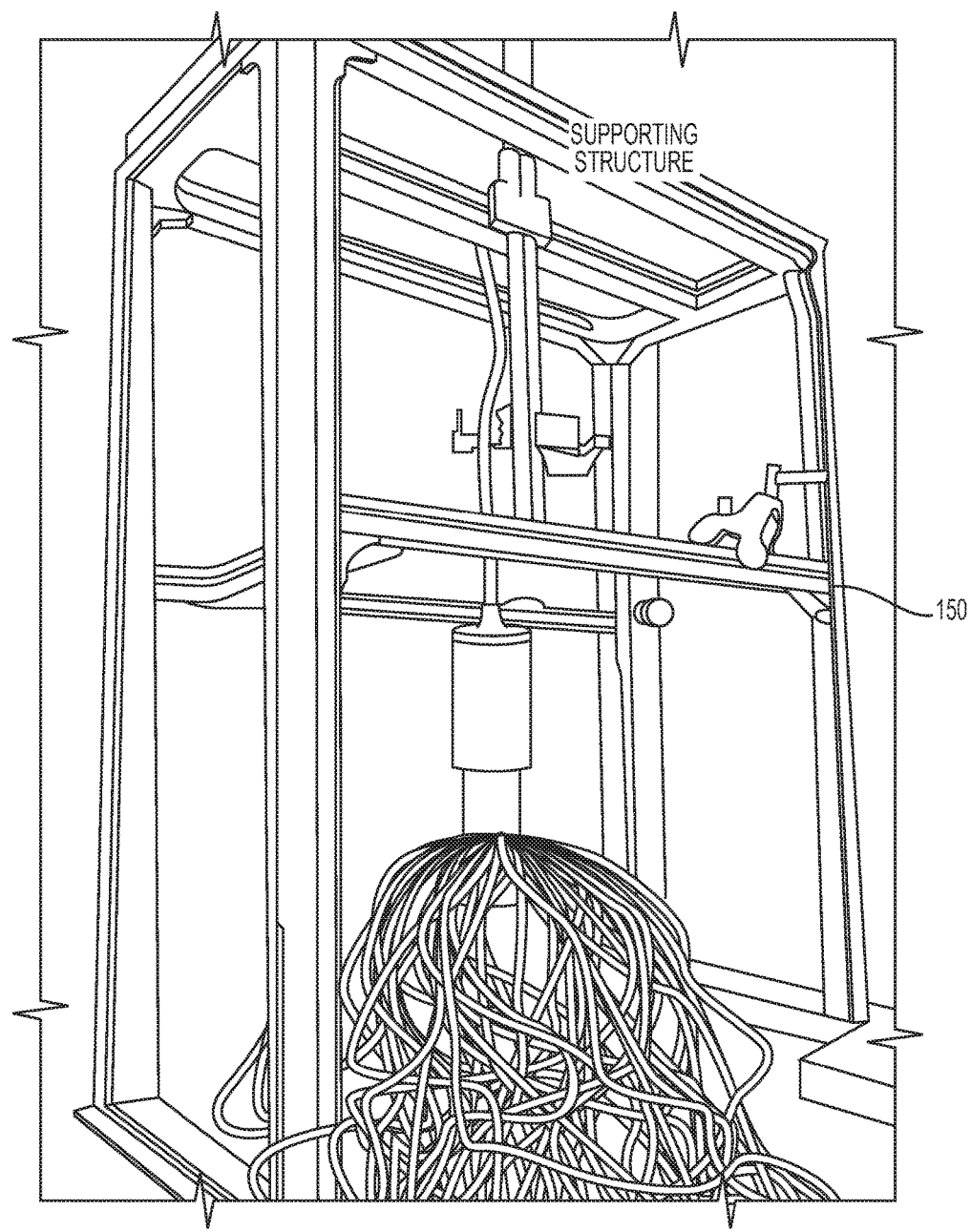

In detail, FIG. 1 is a view illustrating a measurement system according to an embodiment of the inventive concept. FIG. 2 is a view illustrating in detail an xyz micro-translation stage included in the measurement system according to an embodiment of the inventive concept. FIG. 3 is a view illustrating in detail a light dome 110 included in the measurement system according to an embodiment of the inventive concept. FIG. 4 is a view illustrating a support included in the measurement system according to an embodiment of the inventive concept.

Referring to FIGS. 1 to 4, the measurement system according to an embodiment of the inventive concept may necessarily include a light dome 110 having a hemispherical-shaped structure, a macro lens installed camera 120, an xyz micro-translation stage 130, and a measurement unit (not shown). The measurement system may further include a pneumatic vibration isolation unit 140 and a support 150.

The xyz micro-translation stage 130 is arranged below the light dome 110, on which an object is placed. The xyz micro-translation stage 130 moves in xyz-directions to adjust a focal distance between the macro lens installed camera 120 and the object. In this case, the x-direction represents a traversal direction on a plane on which the xyz micro-translation stage 130 is arranged, the y-direction represents a longitudinal direction on a plane on which the xyz micro-translation stage 130 is arranged, and the z-direction represents an orthogonal direction to a plane on which the xyz micro-translation stage 130 is arranged.

In this case, the xyz micro-translation stage 130 may be variously configured to move in the xyz-directions. For example, as shown in FIG. 2, the xyz micro-translation stage 130 may include an xy-translation unit moving in the x and y-directions, and a z-translation unit moving in the z-direction.

In this case, the xyz micro-translation stage 130 may include a slide on which an object is placed and a holder configured to fix the slide on which the object is placed such that the object does not move in the xyz-directions. Thus, when the object to be measured through the measurement system is exchanged, instead of readjusting the measurement system, after the slide is separated from the holder, another slide on which another object is placed is fixed to the holder, so that the object exchanging process may be more simplified.

As shown in FIG. 3, the light dome 110, which has a hemispherical-shaped structure, is arranged over the xyz micro-translation stage 130 and includes hundreds of LEDs at the compactness of a preset interval such that light is radiated to the object (which is an object placed on the xyz micro-translation stage 130) placed therein.

For example, the light dome 110 may include 374 white LEDs (each of which has a diameter of 3 mm) at the density of an interval of 7 degrees to prevent shadow from being casted upon the object and may be formed in a hemispherical shaped structure having a radius of 40 mm.

In this case, the light dome 110 is formed at the center thereof with a hole to allow the macro lens installed camera 120 to photograph the object placed in the light dome 110 through the hole.

Specifically, each of the several hundred LEDs of the light dome 110 may be controlled to be at plural levels to configure a light of spherical harmonics (SH) illumination and may be coupled to a piano-concave lens (which has a flat surface on one surface and a concave surface on the other) to be used as a point light for point-wise illumination.

For example, the several hundred LEDs of the light dome 110 may be configured to be elevated to level 3 of 4095 luminance. Thus, the light dome 110 may include an Arduino microcontroller and a plurality of TLC5940 chips for providing 12-bit 16 channels and a pulse width output.

The macro lens installed camera 120 is arranged over the light dome 110 to photograph an object under the lighting environment in which the light dome 110 radiates light to the object through the hole formed at the center of the light dome 110.

For example, the macro lens installed camera 120 may be implemented by attaching a three-color machine vision camera (for example, Point Grey Grasshopper3: GS3-U3-120S6C-C) 121 having a resolution of 4240×2824 (12 MP, Pixel Pitch of 3.1 μm) to a commercial DSLR macro lens 122 (for example, Canon MP-E 65 mm f/2.8) having a magnification of 5:1 through a C-mount adaptor.

In this case, since the macro lens installed camera 120 is fixed to be close to the hole formed at the center of the light dome 110, as described above, the measurement system of the embodiment may allow the xyz micro-translation stage 130, on which the object is placed, to move in the xyz-directions to adjust the focal distance instead of allowing the macro lens installed camera 120 to move to adjust the focal distance.

The pneumatic vibration isolation unit 140 is arranged below the xyz micro-translation stage 130 to prevent at least one of the light dome 110, the macro lens installed camera 120 and the xyz micro-translation stage 130 from generating a vibration. In this case, as the pneumatic vibration isolation unit 140, a commercial optical table (for example, Daeil DVIO-B2410M-200T) having air vibration isolation may be used.

The macro lens installed camera 120 is attached to the support 150 and the pneumatic vibration isolation unit 140 may be fixed to the support 150. For example, as shown in FIG. 4, the support 150 may be manufactured at a size of 80*40*110 cm and the macro lens installed camera 120 may be attached to an upper frame of the support 150. The pneumatic vibration isolation unit 140 may be fixed to a lower frame of the support 150.

The measurement unit is provided at one side of the measurement system (for example, the measurement unit is embedded in the macro lens installed camera 120) to control the light dome 110 and the macro lens installed camera 120, such that the measurement unit photographs the object under the environment in which the light dome 110 radiates light to obtain a microscale image and simultaneously measures the surface normal vector and the surface reflection function of the object based on the microscale image.

For example, the measurement unit controls the light dome 110 such that the SH illumination and the pointwise illumination are implemented. Thus, the measurement unit may obtain the microscale image by photographing the object under the SH illumination and the pointwise illumination and may simultaneously measure the surface normal vector and the surface reflection function of the object based on the microscale image. This will be described in detail with reference to FIG. 6.

In addition, before obtaining the microscale image by photographing the object to simultaneously measure the surface normal vector and the surface reflection function of the object (before photographing the object), the measurement unit may correct the position of the LEDs of the light dome 110 and the axis of the macro lens installed camera 120 with respect to a surface of the xyz micro-translation stage 130. This will be described in detail with reference to FIG. 5.

As described above, the measurement system according to an embodiment of the inventive concept includes the light dome 110 including hundreds of LEDs, the macro lens installed camera 120 and the xyz micro-translation stage 130, such that the measurement system may simultaneously measure the surface normal vector and the surface reflection function of an object, where each of the LEDs is adjusted to plural levels to implement SH illumination and coupled to a plano-concave lens to be used as a point light for implementing point-wise illumination. Thus, the measurement complexity may be reduced and the measurement accuracy may be improved. In addition, the over-suitability of the measurement process may be reduced.

In addition, the measurement system described above may be applied to a microscope camera system so that the measurement system is used for the processes of capturing and reconstructing an object having various appearances.

Figure 5:
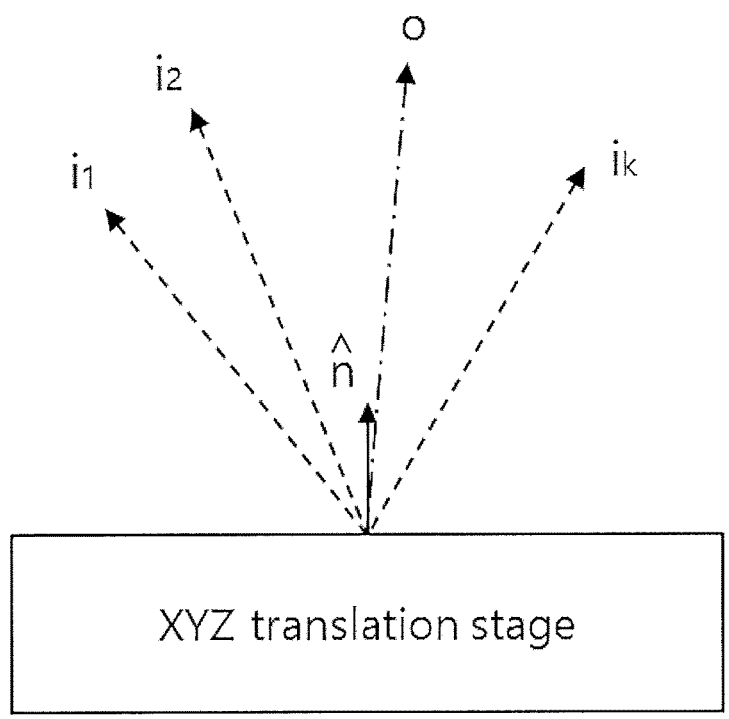
FIG. 5 is a view illustrating a process of correcting a position of an LED of a light dome and an axis of a macro lens installed camera with respect to a surface of an xyz micro-translation stage on a microscale image, according to an embodiment of the inventive concept.

FIG. 5 is a view illustrating a process of correcting a position of an LED of a light dome and an axis of a macro lens installed camera with respect to a surface of an xyz micro-translation stage on a microscale image, according to an embodiment of the inventive concept.

Referring to FIG. 5, before obtaining the microscale image by photographing an object to simultaneously measure the surface normal vector and the surface reflection function of the object (before photographing the object), the measurement unit included in the measurement system according to an embodiment may control the light dome and the macro lens installed camera such that the measurement unit corrects the positions of the LEDs of the light dome and the axis of the macro lens installed camera with respect to the surface of the xyz micro-translation stage on the microscale image to be photographed.

For example, the measurement unit may correct the positions of the LEDs of the light dome with respect to the macro lens installed camera and may correct the normal vector of the xyz micro-translation stage with respect to the macro lens installed camera. In addition, the measurement unit may transform the view direction of the macro lens installed camera and the vector of light radiated from the light dome to the reference coordinate system of the xyz micro-translation stage, so that the measurement unit corrects the positions of the LEDs of the light dome with respect to the surface of the xyz micro-translation stage and the axis of the macro lens installed camera.

In more detail, for example, the measurement unit may first allow the several hundred LEDs of the light dome to be selectively turned on such that light is radiated to a chrome ball (having a diameter of 1.0 mm) used as a light probe and placed on the xyz micro-translation stage. Then, the measurement unit may control the macro lens installed camera such that a microscale test image is obtained by photographing the chrome ball.

Thus, the measurement unit ma calculate an initial light vector $\hat{i_k}$ according to the mirror reflection equation $\hat{i_k}$ =2( $\widehat{n_k}\cdot \hat{o})\widehat{n_k} -\hat{o}$, where $\hat{o}$ may represent a vector $[0, 0, 1]^T$ in the initial view direction in the coordinate system of the macro lens installed camera, $\widehat{n_k}$ may be a value (which is a value corresponding to the direction of the vector $\hat{o}$ in the initial view direction) corresponding to a normal of the most brightness pixel on the chrome ball surface in the coordinate system of the macro lens installed camera.

Then, as shown in FIG. 5, the measurement unit obtains the direction f of the xyz micro-translation stage in the coordinate system of the macro lens installed camera based on the information about average shaded light of each light. In this case, the measurement unit may measure 'n̂' in dependence on photometric stereo.

Thereafter, the measurement unit may transform the coordinates of the macro lens installed camera to a reference coordinate system of the xyz micro-translation stage with respect to the same z-direction component of n̂ and an orthogonal vector frame. In this case, the measurement unit may transform the vector ô in the initial view direction in the coordinate system of the macro lens installed camera to the vector 'o' in a real view direction in the reference coordinate system of the xyz micro-translation stag by applying rotation transform on the vector frame.

Figure 6:
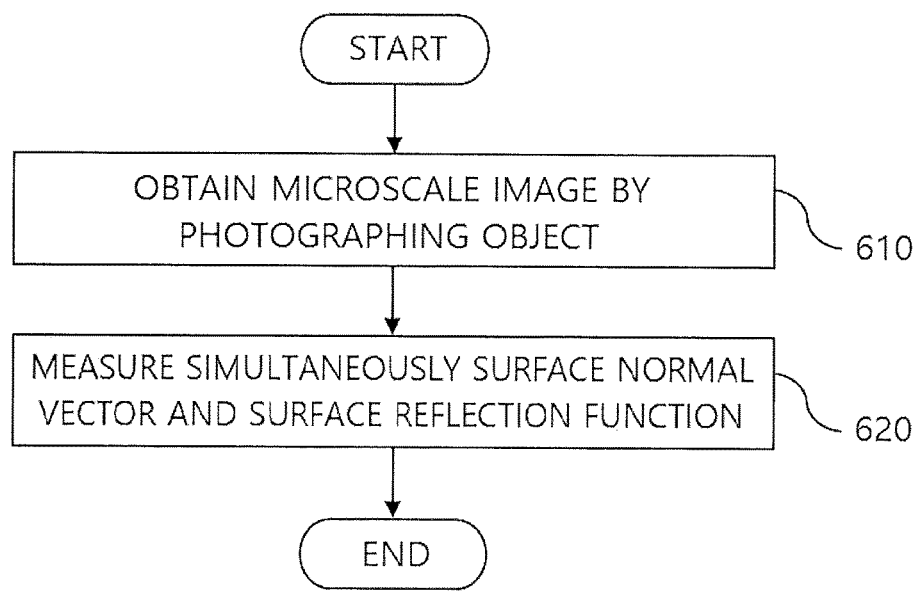
FIG. 6 is a flowchart illustrating a method of simultaneously measuring a surface normal vector and a surface reflection function in microscale according to an embodiment of the inventive concept.

FIG. 6 is a flowchart illustrating a method of simultaneously measuring a surface normal vector and a surface reflection function in microscale according to an embodiment of the inventive concept. As described below, the method of simultaneously measuring a surface normal vector and a surface reflection function in microscale is performed by the measurement system (specifically, the measurement unit included in the measurement system) described above. In addition, the method of simultaneously measuring a surface normal vector and a surface reflection function in microscale may be implemented with a computer program recorded in media coupled to a computer for implementing the measurement system described above.

Referring to FIG. 6, in step 610, the measurement system according to an embodiment controls the light dome and the macro lens installed camera such that a microscale image is obtained by photographing an object under the light environment in which the light dome radiates light.

In detail, in step 610, the measurement system may obtain the microscale image by photographing an object under the spherical harmonics illumination of the light dome and the pointwise illumination that uses at least some LEDs of the light dome as point lights.

Then, in step 620, the measurement system simultaneously measures the surface normal vector and the surface reflection function of the object based on the microscale image.

In step 620, the measurement system may calculate the surface normal vector of the object by using the SfS scheme based on the microscale image.

In this case, since the hole is formed at the center of the light dome (any LEDs are not formed at the center of the light dome), a part of a pattern of spherical harmonics illumination may be omitted in step 610, so that a partial value included in the surface normal vector may tend to be fixed.

Thus, to solve the problem, the measurement system updates the fixed partial value included in an initial surface normal vector and an outlier artifact to calculate the surface normal vector by inserting a mirror-like reflection vector by the point light into the initial surface normal vector.

For example, the measurement system may measure each initial surface normal vector per pixel of the object in the microscale image and may update the initial surface normal vector by using the SfS scheme based on the mirror-like reflection vector by the point light to calculate the surface normal vector of the object.

In addition, in step 620, the measurement system may calculate the surface reflection function (Spatially-Varying Bidirectional Reflectance Distribution Functions: SVBRDFs) of the object, based on the surface normal vector calculated above, the normal distribution function (NDF) term of the reflectance of the object expressed as a non-parametric function, a geometric structure term representing shadowing/masking effects of the light emitted from the light dome in the view direction of the macro lens installed camera, and a Fresnel term concerned with a color vector.

For example, in consideration of the fixed view direction of the macro lens installed camera, the measurement system may represent each of BRDFs in SVBRDFs as the diffusion term and the non-parametric reflection term. The measurement system may factor the reflectance of the object with a mixture coefficient corresponding to reference BRDFs after optimizing the non-parametric reflection term, such that the measurement system calculates the surface reflection function of the object.

In more detail, for example, the light reflected at point x of the object in view direction o under light I may be expressed as following Equation 1.

$$L(x,o)=R(x,o,i)(n\cdot i)L(x,i) \qquad \text{<Equation 1>}$$

In Equation 1, 'n' represents a surface normal vector at point x. In addition, the reflectance R of the object may include a diffusion term and a regular reflection term and may be expressed as following Equation 2.

$$R(x, o, i) = \frac{1}{\pi}\rho_d(x) + \rho_s(x)\frac{D(x, h)G(n, o, i)F(x, h, i)}{4(n\cdot o)(n\cdot i)} \qquad \text{< Equation 2 >}$$

In Equation 2, $\rho_d(x)$ and $\rho_s(x)$ represent the diffusion and reflection albedo of point x in microfacet scale, respectively, h=(o+i)/|o+i| represents a half of an angle, 'D' represents an NDF term of the reflectance of the object represented as a non-parametric function, 'G' represents a geometric structure term representing a shadowing/masking effect of the light emitted from the light dome in the view direction of the macro lens installed camera, and 'F' represents a Fresnel term concerned with a color vector.

In this case, the NDF term may be expressed as the non-parametric function made with a table of 90 coefficients. The measurement unit may factor a reflection lobe of the object with a single nonparametric NDF term in monotonicity constraint.

Since the geometric structure term expressed in Ashikhmin's formula relates to the NDF term in the formula, after obtaining the initial geometric structure term based on a V-grooves scheme, the measurement unit may mutually optimize the geometric structure term and the NDF term to factor the geometric structure term and the NDF term.

To reduce the complexity of the process of calculating the surface reflection function, the Fresnel term may be simplified with color vector constant F from the color vector F(x,h,i).

That is, after repeatedly optimizing the NDR term and the geometric structure term of the reflectance R, the measurement unit may factor the NDR term and the geometric structure term to update the surface reflection function. In this case, the repetitive optimization of the NDR term and the geometric structure term may be performed until a root mean squared error (RMSE) is increased to a reference value or more.

In addition, although not shown, before performing step 610, the measurement system may control the light dome and the macro lens installed camera, so that the measurement system corrects the positions of the LEDs of the light dome with respect to the surface of the xyz micro-translation stage and the axis of the macro lens installed camera on the microscale image to be photographed.

For example, the measurement system may correct the positions of the LEDs of the light dome with respect to the macro lens installed camera and may correct the normal vector of the xyz micro-translation stage with respect to the macro lens installed camera. In addition, the measurement system may transform the view direction of the macro lens installed camera and the vector of light radiated from the light dome to the reference coordinate system of the xyz micro-translation stage, so that the measurement system corrects the positions of the LEDs of the light dome with respect to the surface of the xyz micro-translation stage and the axis of the macro lens installed camera.

As described above, the measurement system according to an embodiment of the inventive concept includes the light dome including hundreds of LEDs, the macro lens installed camera and the xyz micro-translation stage, such that the measurement system may obtain the microscale image by photographing an object under SH illumination of the light dome and point wise illumination and may simultaneously measure the surface normal vector and the surface reflection function of an object, where each of the LEDs is adjusted to plural levels to implement the SH illumination and coupled to a plano-concave lens to be used as a point light for implementing the point-wise illumination. Thus, the measurement complexity may be reduced and the measurement accuracy may be improved. In addition, the over-suitability of the measurement process may be reduced.

In addition, the measurement system described above may be applied to systems for capturing the appearances of various objects such as microscope camera systems.

The above-described devices may be realized by hardware elements, software elements and/or combinations thereof. For example, the devices and elements illustrated in the exemplary embodiments of the inventive concept may be implemented in one or more general-use computers or special-purpose computers, such as a processor, a controller, an arithmetic logic unit (ALU), a digital signal processor, a microcomputer, a field programmable gate array (FPGA), a programmable logic unit (PLU), a microprocessor or any device which may execute instructions and respond. A processing unit may implement an operating system (OS) or one or software applications running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements. For example, the processing unit may include a plurality of processors or one processor and one controller. In addition, the processing unit may have a different processing configuration, such as a parallel processor.

Software may include computer programs, codes, instructions or one or more combinations thereof and may configure a processing unit to operate in a desired manner or may independently or collectively control the processing unit. Software and/or data may be permanently or temporarily embodied in any type of machine, components, physical equipment, virtual equipment, computer storage media or units so as to be interpreted by the processing unit or to provide instructions or data to the processing unit. Software may be dispersed throughout computer systems connected via networks and may be stored or executed in a dispersion manner. Software and data may be recorded in one or more computer-readable storage media.

The methods according to the above-described exemplary embodiments of the inventive concept may be implemented with program instructions which may be executed through various computer means and may be recorded in computer-readable media. The media may also include, alone or in combination with the program instructions, data files, data structures, and the like. The program instructions recorded in the media may be designed and configured specially for the exemplary embodiments of the inventive concept or be known and available to those skilled in computer software. Computer-readable media include magnetic media such as hard disks, floppy disks, and magnetic tape; optical media such as compact disc-read only memory (CD-ROM) disks and digital versatile discs (DVDs); magneto-optical media such as floptical disks; and hardware devices that are specially configured to store and perform program instructions, such as read-only memory (ROM), random access memory (RAM), flash memory, and the like. Program instructions include both machine codes, such as produced by a compiler, and higher level codes that may be executed by the computer using an interpreter.

While a few exemplary embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

Thus, it is intended that the inventive concept covers other realizations and other embodiments of this inventive concept provided they come within the scope of the appended claims and their equivalents.

What is claimed is:

1. A method of simultaneously measuring a surface normal vector and a surface reflection function in microscale, wherein the method is performed through a system for simultaneously measuring the surface normal vector and the surface reflection function in microscale, wherein the system comprises:
a light dome having a hemispherical-shaped structure and including a plurality of LEDs at a preset interval to radiate light to an object placed therein; and
a macro lens installed camera arranged over the light dome to photograph the object through a hole formed at a center of the light dome under an environment in which a light is radiated from the light dome; and wherein the method comprises:
obtaining a microscale image by controlling the light dome and the macro lens installed camera, wherein the microscale image is obtained by photographing the object under the environment in which the light is radiated from the light dome, and wherein the obtaining of the microscale image comprises obtaining the microscale image by photographing the object under spherical harmonics (SH) illumination of the light dome and pointwise illumination which uses at least one of the LEDs of the light dome as a point light; and simultaneously measuring a surface normal vector and a surface reflection function of the object based on the microscale image, wherein the measuring of the surface normal vector and the surface reflection function comprises calculating the surface normal vector of the object by using a shape-from-specular scheme based on the microscale image, and wherein the measuring of the surface normal vector and the surface reflection function further comprises calculating the surface reflection function of the object, based on the calculated surface normal vector, a normal distribution function term of reflectance of the object expressed as a non-parametric function, a geometric structure term representing shadowing/masking effects of the light emitted from the light dome in a view direction of the macro lens installed camera, and a Fresnel term concerned with a color vector.

2. A method of simultaneously measuring a surface normal vector and a surface reflection function in microscale, wherein the method is performed through a system for simultaneously measuring the surface normal vector and the surface reflection function in microscale, wherein the system comprises:
a light dome having a hemispherical-shaped structure and including a plurality of LEDs at a preset interval to radiate light to an object placed therein;
a macro lens installed camera arranged over the light dome to photograph the object through a hole formed at a center of the light dome under an environment in which a light is radiated from the light dome; and
an xyz micro-translation stage arranged under the light dome and configured to move in xyz-directions to adjust a focal distance between the macro lens installed camera and the object, wherein the object is placed on the xyz micro-translation stage, and wherein the method comprises:
obtaining a microscale image by controlling the light dome and the macro lens installed camera, wherein the microscale image is obtained by photographing the object under the environment in which the light is radiated from the light dome, and wherein the obtaining of the microscale image comprises obtaining the microscale image by photographing the object under spherical harmonics (SH) illumination of the light dome and pointwise illumination which uses at least one of the LEDs of the light dome as a point light; and simultaneously measuring a surface normal vector and a surface reflection function of the object based on the microscale image, wherein the measuring of the surface normal vector and the surface reflection function comprises calculating the surface normal vector of the object by using a shape-from-specular scheme based on the microscale image, and wherein the measuring of the surface normal vector and the surface reflection function further comprises calculating the surface reflection function of the object, based on the calculated surface normal vector, a normal distribution function term of reflectance of the object expressed as a non-parametric function, a geometric structure term representing shadowing/masking effects of the light emitted from the light dome in a view direction of the macro lens installed camera, and a Fresnel term concerned with a color vector.

3. A computer program stored in a non-transitory computer readable medium which is coupled to a computer for implementing a system for simultaneously measuring a surface normal vector and a surface reflection function in microscale to execute a method of simultaneously measuring the surface normal vector and the surface reflection function in microscale, wherein the system comprises:
a light dome having a hemispherical-shaped structure and including a plurality of LEDs at a preset interval to radiate light to an object placed therein; and
a macro lens installed camera arranged over the light dome to photograph the object through a hole formed at a center of the light dome under an environment in which a light is radiated from the light dome; and wherein the method comprises:
obtaining a microscale image by controlling the light dome and the macro lens installed camera, wherein the microscale image is obtained by photographing the object under the environment in which the light is radiated from the light dome, and wherein the obtaining of the microscale image comprises obtaining the microscale image by photographing the object under spherical harmonics (SH) illumination of the light dome and pointwise illumination which uses at least one of the LEDs of the light dome as a point light; and simultaneously measuring a surface normal vector and a surface reflection function of the object based on the microscale image, wherein the measuring of the surface normal vector and the surface reflection function comprises calculating the surface normal vector of the object by using a shape-from-specular scheme based on the microscale image, and wherein the measuring of the surface normal vector and the surface reflection function further comprises calculating the surface reflection function of the object, based on the calculated surface normal vector, a normal distribution function term of reflectance of the object expressed as a non-parametric function, a geometric structure term representing shadowing/masking effects of the light emitted from the light dome in a view direction of the macro lens installed camera, and a Fresnel term concerned with a color vector.

4. A computer program stored in a non-transitory computer readable medium which is coupled to a computer for implementing a system for simultaneously measuring a surface normal vector and a surface reflection function in microscale to execute a method of simultaneously measuring the surface normal vector and the surface reflection function in microscale, wherein the system comprises:
a light dome having a hemispherical-shaped structure and including a plurality of LEDs at a preset interval to radiate light to an object placed therein;
a macro lens installed camera arranged over the light dome to photograph the object through a hole formed at a center of the light dome under an environment in which a light is radiated from the light dome; and
an xyz micro-translation stage arranged under the light dome and configured to move in xyz-directions to adjust a focal distance between the macro lens installed camera and the object, wherein the object is placed on the xyz micro-translation stage, and wherein the method comprises:
obtaining a microscale image by controlling the light dome and the macro lens installed camera, wherein the microscale image is obtained by photographing the object under the environment in which the light is radiated from the light dome, and wherein the obtaining of the microscale image comprises obtaining the microscale image by photographing the object under spherical harmonics (SH) illumination of the light dome and pointwise illumination which uses at least one of the LEDs of the light dome as a point light; and simultaneously measuring a surface normal vector and a surface reflection function of the object based on the microscale image, wherein the measuring of the surface normal vector and the surface reflection function comprises calculating the surface normal vector of the object by using a shape-from-specular scheme based on the microscale image, and wherein the measuring of the surface normal vector and the surface reflection function further comprises calculating the surface reflection function of the object, based on the calculated surface normal vector, a normal distribution function term of reflectance of the object expressed as a non-parametric function, a geometric structure term representing shadowing/masking effects of the light emitted from the light dome in a view direction of the macro lens installed camera, and a Fresnel term concerned with a color vector.

* * * * *